United States Patent [19]

Buirge

[11] Patent Number: 5,735,897
[45] Date of Patent: Apr. 7, 1998

[54] INTRAVASCULAR STENT PUMP

[75] Inventor: Andrew W. Buirge, Minneapolis, Minn.

[73] Assignee: SciMed Life Systems, Inc., Maple Grove, Minn.

[21] Appl. No.: 775,618

[22] Filed: Jan. 2, 1997

Related U.S. Application Data

[63] Continuation of Ser. No. 639,381, Apr. 26, 1996, abandoned, which is a continuation of Ser. No. 300,742, Sep. 2, 1994, abandoned, which is a continuation-in-part of Ser. No. 138,923, Oct. 19, 1993, abandoned.

[51] Int. Cl.$^6$ ................................. A61F 2/04; A61F 2/06
[52] U.S. Cl. ............................ 623/12; 623/11; 623/1
[58] Field of Search ............................ 623/1, 11, 12; 600/36; 606/191, 194, 195, 198; 604/892.1

[56] References Cited

U.S. PATENT DOCUMENTS

| | | |
|---|---|---|
| 3,056,408 | 4/1962 | Brown . |
| 4,219,520 | 8/1980 | Kline . |
| 4,230,119 | 10/1980 | Blum . |
| 4,404,971 | 9/1983 | LeVeen et al. . |
| 4,503,569 | 3/1985 | Dotter . |
| 4,520,823 | 6/1985 | LeVeen et al. . |
| 4,763,653 | 8/1988 | Rockey . |
| 4,776,337 | 10/1988 | Palmaz . |
| 4,795,458 | 1/1989 | Regan . |
| 4,806,595 | 2/1989 | Noishiki et al. . |
| 4,820,298 | 4/1989 | Leveen et al. . |
| 4,830,003 | 5/1989 | Wolff et al. . |
| 4,832,688 | 5/1989 | Sagae et al. . |
| 4,840,690 | 6/1989 | Melinyshyn et al. . |
| 4,877,030 | 10/1989 | Beck et al. . |
| 4,879,135 | 11/1989 | Greco et al. . |
| 4,886,062 | 12/1989 | Wiktor . |
| 4,900,303 | 2/1990 | Lemelson . |
| 4,902,289 | 2/1990 | Yannas . |
| 4,922,905 | 5/1990 | Strecker . |
| 4,923,464 | 5/1990 | DiPisa, Jr. . |
| 4,929,240 | 5/1990 | Kirsch et al. . |
| 4,950,227 | 8/1990 | Savin et al. . |
| 4,969,890 | 11/1990 | Sugita et al. . |
| 5,015,253 | 5/1991 | MacGregor . |
| 5,019,090 | 5/1991 | Pinchuk . |
| 5,028,597 | 7/1991 | Kodama et al. . |
| 5,037,427 | 8/1991 | Harada et al. . |
| 5,041,126 | 8/1991 | Gianturco . |
| 5,057,321 | 10/1991 | Edgren et al. ........................ 604/892.1 |
| 5,059,211 | 10/1991 | Stack et al. . |
| 5,061,281 | 10/1991 | Mares et al. . |
| 5,078,736 | 1/1992 | Behl . |
| 5,085,629 | 2/1992 | Goldberg et al. . |
| 5,089,005 | 2/1992 | Harada . |
| 5,092,839 | 3/1992 | Kipperman . |
| 5,092,841 | 3/1992 | Spears . |
| 5,092,877 | 3/1992 | Pinchuk . |
| 5,100,429 | 3/1992 | Sinofsky et al. . |
| 5,102,417 | 4/1992 | Palmaz . |
| 5,104,403 | 4/1992 | Brotzu et al. .............................. 623/1 |
| 5,116,360 | 5/1992 | Pinchuk et al. . |
| 5,201,778 | 4/1993 | Brotzu et al. . |
| 5,207,705 | 5/1993 | Trudell et al. .............................. 623/1 |
| 5,304,121 | 4/1994 | Sahatjian ............................ 606/194 |
| 5,411,550 | 5/1995 | Herweck et al. ........................ 623/1 |
| 5,413,572 | 5/1995 | Wong et al. ........................ 604/892.1 |

FOREIGN PATENT DOCUMENTS

| | | |
|---|---|---|
| 0 157 178 A1 | 10/1985 | European Pat. Off. . |
| 382158A | 8/1990 | European Pat. Off. . |
| 0 604 022 A1 | 6/1994 | European Pat. Off. . |
| 3627 487 A1 | 2/1988 | Germany . |
| 60-190966 | 9/1985 | Japan . |
| 63-97158 | 4/1988 | Japan . |

OTHER PUBLICATIONS

Dilution-Diffusion Osmotic Pumping, K.J. Himmelstein, *Proceed.Intern.Symp.Control.Rel.Bioact.Mater.*, 19(1992), Controlled Release Society, Inc. p. 10–11.

*Primary Examiner*—Debra S. Brittingham
*Attorney, Agent, or Firm*—Vidas, Arrett & Steinkraus

[57] ABSTRACT

A multi-layer vascular therapeutic-containing prosthesis designed and arranged to "pump" the therapeutics into the blood stream.

58 Claims, 1 Drawing Sheet

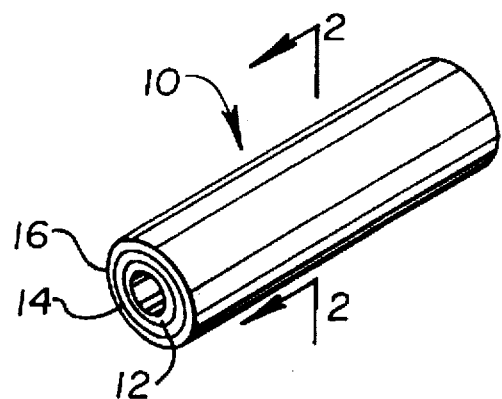
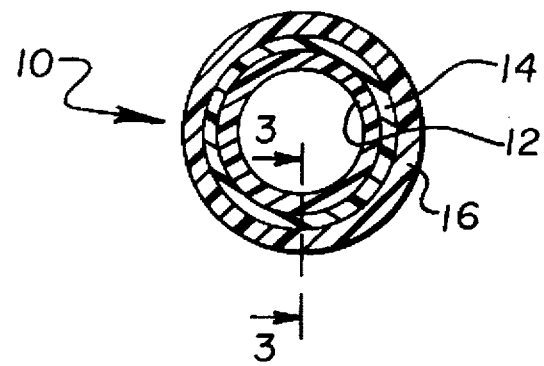
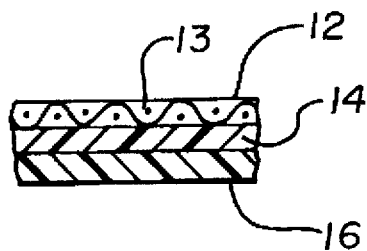

INTRAVASCULAR STENT PUMP

CROSS REFERENCE TO RELATED APPLICATION

This application is a continuation-in-part of application Ser. No. 08/138,923, filed Oct. 19, 1993, now abandoned the disclosure of which is hereby incorporated by reference, which is a continuation of application Ser. No. 08/300,742, filed Sep. 24, 1994, now abandoned, which is a continuation-in-part of application Ser. No. 08/138,923, filed Oct. 19, 1993, now abandoned.

BACKGROUND OF THE INVENTION

1. Field of the Invention

This invention relates to a multi-layer vascular therapeutic-containing prothesis designed and arranged to "pump" the therapeutics into the blood stream.

2. Description of Related Art

Japanese Patent Application J63-97158A published Apr. 27, 1988 discloses an artificial blood vessel having heparin in the pores of an inner wall sealed with a water-swelling polymer. Polyurethane is used as a continuous cell structure. The tubular structure is treated with heparin and a water-swelling polymer such as polyvinylpyrrolidone, polyethylene glycol, polyacrylic acid or the like.

U.S. Pat. No. 5,085,629 issued to Goldberg et al on Feb. 4, 1992 discloses a resorbable stem comprising a terpolymer of: L(-)lactide, glycolide, and epsilon caprolactone.

European Patent 382158A published on Aug. 16, 1990 describes an implantable prothesis comprising an absorbable layer 3, a permeable support layer 4 and another permeable layer 2 (page 5, lines 8–20). Absorbable polyesters include polylactate, polyglycolate and poly-E-caprolactone ester, (page 6, lines 5–8). A tube of copolymer of polylactate and polyglycolate containing heparin (in sustained release form) can be cast from solution onto the surface of a silicone tube to serve as an anti-thrombotic artificial blood vessel (page 7, lines 20–27).

U.S. Pat. No. 5,201,778 issued to Brotzu et al on Apr. 13, 1993 discloses a vascular prothesis comprising a spindle between a prothesis 1 and prosthesis 3 in which microcapsules are placed (Col. 2, lines 23–28). In such a vascular prosthesis, the hematic flow allows for the circulation of the hormones secreted by the cells (Col. 2, lines 36–40).

The prior art discloses resorbable stents made of polymers, e.g. polylactides, polyglycolates and caprolactones. U.S. Pat. No. 5,085,629 is an example. A water swelling polymer e.g. polyvinylpyrrolidone, serving in an artificial blood vessel as a drug releasing wall of the vessel is shown in J63-97158A. The use of a collagen as a supportive wall in an implanted artificial blood vessel is disclosed in U.S. Pat. No. 5,028,597 for example.

SUMMARY OF THE INVENTION

The prior art does not disclose the stent-like construction and arrangement of the subject invention in which an inner porous support layer and an outer support layer trap and hold therebetween a swellable drug or therapeutic-containing layer.

BRIEF DESCRIPTION OF THE FIGURES

FIG. 1 is a schematic showing of the stent-like vascular prosthesis according to the invention.

FIG. 2 is a cross-section view of the prosthesis of FIG. 1 taken along line 2—2.

FIG. 3 is a cross-section of the prosthesis of FIG. 1 taken along line 3—3 of FIG. 2, showing alternate forms of the invention.

DETAILED DESCRIPTION OF THE INVENTION

The characteristics and advantages of the vascular prosthesis of the invention will be better understood from the following detailed description.

In its most preferred form, the stent-like construction comprises an intravascular, resorbable, UV curable drug delivery stent-pump in the form of a multi-layer cylindrical device constructed and arranged for implantation in a blood vessel or other duct or body passage. An inner polymeric layer and an outer polymeric layer support therebetween a swellable drug or therapeutic layer.

The stent-pump in this form is UV curable in situ to allow it to stay in the expanded state upon placement and expansion in a vessel. If the device was not cured upon deployment or implantation following expansion it would simply shrink back down to its pre-expanded size. The material, without curing, behaves much like a rubber band. The device can be cured or rather "rigidified" in situ by means other than UV light. These other means may be:

1. Exposure to a chemical that can initiate polymerization. Micro spheres which can contain a peroxide or strong acid may be dispersed throughout the inner and outer layers. Upon expansion of the device, these spheres would rupture, thus releasing the materials which effect the cure.
2. Heat may also be employed to effect the cure. Heat sensitive initiators are stable at room temperature, but when exposed to elevated temperatures they decompose into fragments which may spontaneously start a polymerization.

The stent-pump is implanted via a modified balloon angioplasty catheter (not shown). The modification which needs to be made to a standard catheter is the fitting of the device with an optical fiber which is used to deliver the UV energy to the stent-pump, effecting the cure. An optical fiber (as well as the use of UV light) would not be necessary with the use of the "micro sphere technology". Optical fibers on catheters are known in the art. Inflation of the balloon expands the stent-pump cylindrical diameter which is then held in place until cured by the UV radiation or other curing means. The balloon is then deflated and the catheter is removed, leaving the expanded stent-pump in place.

The stent-pump of this embodiment is shown in FIGS. 1 and 2. It is cylindrical in form, the OD being selected to correspond substantially to the ID of the implantation site. Obviously, the device can be made in various selected sizes. The cylindrical structure generally designated at 10 is comprised of at least three layers, an inner layer 12, an intermediate layer 14, and an outer layer 16, and is arranged so that blood can flow through its inner diameter when implanted in a blood vessel. In this way blood being exposed to the permeable inner layer 12 can diffuse through it and into layer 14. The intermediate layer 14 is made up of a blood-swellable material. As it swells between the binding layers 12 and 16 upon absorbing blood in layer 14, it is subjected to a squeezing action. This pump-like action tends to force any drug or other therapeutic contained in layer 14 through the porous layer 12 and into the blood stream. As already indicated, most preferably layers 12 and 14 are of polymeric material, although other materials may be used as is discussed hereinbelow.

As well as pumping, there is a diffusion process which occurs to liberate drug from the device. The actual dynamics of drug release can be described by two mechanisms. First of all, the intermediate layer would swell, then the drug/polymer mixture would be forced out. After the pressures equalize, the remainder of the drug/polymer would elute out of the device via a diffusion mechanism. The terms "stent-pump" and "pump" or "pumping" are used herein in this sense.

The inner layer 12 is porous or perforated or otherwise permeable to allow contact between the blood or other fluid flowing through the device and the intermediate layer 14 as well as to allow diffusion therethrough and into the blood stream or the like of the therapeutic and fluid squeezed from layer 14 as a result of its swelling between layers 12 and 16. The inner layer, when polymeric, can be made porous by one of several methods. One method involves scoring, or nicking the inner material. Upon expansion, the scored or nicked areas will stretch to the point of rupture, thus causing an open space. Another method involves the incorporation of a microcrystalline, water soluble material into the inner layer. Upon expansion, the material will be exposed to the flow of blood, and the water soluble portion will dissolve. The ensuing voids provide the pore structure which is necessary for blood to contact and swell the middle layer of the device.

Layers 12 and 16 for the most preferred embodiment may be comprised of, for example, polylactics, polyacetates, polyacrylates, polyglycol and/or polycaprolactones. Layer 16 may also be comprised of collagen, for example. The polymers that comprise a portion of layers 12 and 16 are preferably polyester, polyether, polyamide, or a mixture thereof. The specific polymer which was used in the initial prototypes was poly-D,L-Lactic acid. In addition to the foregoing, layer 16 will preferably include photocure or heat curable additives to render layer 16 hardenable such as by heat or UV. A list of materials which can be used to render layer 16 hardened or rigid is provided in the Table below. The reason why this is necessary is because the actual support of the device is provided by layer 16. The rigid layer 16 not only provides structural integrity to the device but can also act as a stent, keeping a narrowed artery wall open. For example, layer 16 might be comprised of poly-D,L-lactic acid, ethylene glycol dimethacrylate and the photoinitiator 2-hydroxy-2-methyl-1-propanone.

TABLE 1

Ethylene glycol dimethacrylate
Cyclohexylmethacrylate
Ethylene glycol diacrylate
Neopentyl glycol diacrylate
Polyethylene glycol (GOO) dimethacrylate
Tripropylene glycol diacrylate
Lauryl methacrylate
Stearyl methacrylate
Ethoxylated bisphenol A dimethacrylate
Ethoxylated bisphenol A diacrylate
Di-Trimethylol propane tetra acrylate (LTx)
Iso decyl acrylate
Dipurt acrythritol penta acrylate
Isobornyl methacrylate
Ethoxylated trionethylol propane triacrylate (LTx)
Highly ethoxylated bisphenol A dimethacrylate
Propoxylated trimethylol propane triacrylate
Tridecyl methacrylate
Ethoxylated pentaerythritol tetra acrylate
caprolactone acrylate
Highly ethoxylated TMPTA
Highly propoxylated TMPTA
Highly ethoxylated TMPTA
Isobornyl acrylate TABLE 1-continued Propoxylated Neopentyl glycol diacrylate
Glyceryl propoxy triacrylate
Highly propoxylated glyceryl triacrylate Intermediate layer 14, the blood or water swelling material, is the drug or therapeutic containing and dispensing matrix and may be comprised of, for example, polyvinylpyrrolidone, polyethylene glycol, polyethylene oxide or polyvinyl alcohol made up in an aqueous solution containing dissolved drug or the like. Any intravenous type drug may be included such as heparin, hirudin, and dextran to name a few. There are a plethora of pharmaceutical agents which may be incorporated into the device (layer 14). These should not be limited to the drugs used for heart/angioplasty purposes. One use of this device may be the treatment of local infection, another may be the delivery of antineoplastic agents to a tumor via its main blood supply. Also, the intermediate layer may contain therapeutic agents used to remedy an abnormal condition or disease state. There are many general classes of drugs that can be employed, from analgesics to urinary tract agents, it is difficult to list them all. An original focus was to incorporate thrombolytics such as urokinase or streptokinase, as well as the anticoagulants heparin, dextran or hirudin although this invention is clearly not limited to them.

Since the device provides support to a blood vessel as well as providing controlled release and/or pumping of therapeutics into the blood stream or the like, it is referred to herein as a stent-pump.

The device, in its most preferred form, may be made by preparing separate solutions of the three polymeric compositions selected to form the three layers 12, 14, and 16. A mandrel such as PTFE shrink tubing over a stiff rod is then dip coated by dipping the tubing into the solution of inner layer 12 material, then into the solution for intermediate layer 14 material, then into the solution for outer layer 16 material. Typically, about 14 dips into each solution provides an adequate dip coating of each layer. This will, of course, vary depending on the size of the device desired, the concentration of the solutions, thickness of layers, etc. The dimensions of the finished device may vary from an outside diameter of a fraction of a millimeter up to ca. 1 cm. The teflon mandrel is smaller than the finished device, and would typically be in the range of 0.1-3 mm in outside diameter. The stiff rod would fit easily within the teflon mandrel, being slightly smaller than the teflon heat-shrink tube. In one method of the dip coating technique a long tube of stent-pump is prepared and then individual stents are cut off. These individual stents are then mounted on a separate mandrel and then the ends are dip coated a number of times to seal the intermediate layer.

After hardening or curing of the dip coated laminate structure, it is removed from the mandrel by pulling out the core rod and by pulling on both exposed ends of the shrink tubing simultaneously to break it loose from the inner layer 12.

Another technique for making the device is to cast sheets of each layer onto a smooth surface such as glass. Each sheet may be rolled or wrapped onto the mandrel or tubing successively, each wrapping being accompanied by rolling of the mandrel on a flat surface. The mandrel or tubing is then removed as already described.

In summary, the various components of the most preferred embodiment of the device may be described as follows:

Layer 16—The outer layer may be comprised of a polymer (polyester, polyether, polyamine, etc.) a reactive monomer (see the line 13 list) and a polymerization initiator. The initiator need not be limited to photoreactive materials, but rather materials which can produce radicals or acids upon the delivery of energy to the device.

Layer 14—The intermediate drug bearing layer comprises a mixture of a therapeutic agent in any water (or blood) swelling/dissolving natural or synthetic material. Natural materials may include polysaccharides, or blood serum components. Polyvinyl pyrrolidone, polyethylene glycol, and polyvinyl alcohol (etc.) can be used as synthetic materials.

Layer 12—The inner, bodily fluid contacting layer may be prepared from the same materials as the outer layer except in one case a microcrystalline salt or otherwise water/blood soluble material is added for porosity. These materials can be simple inorganic salts, sugars or polysaccharides.

The preferred materials are as follows:

Layer 16—poly-D,L-lactic acid, ethylene glycol dimethacrylate, and 2-hydroxy-2-methyl-1-phenyl-1-propanone;

Layer 14—polyvinylpyrrolidone, water and sodium heparin; and

Layer 12—identical to layer 16 with the addition of micro crystalline (sub micron to micron particle size) sodium heparin.

As already indicated, the preferred form of the invention is an expandable stent-like structure which may be expanded in situ to fit the vessel in which it is being placed. However, a stent-like structure of fixed diameter may also make use of the invention. In such an instance, stent pumps of various diameter would be available so that a vessel of particular diameter could be accommodated by selecting the nearest and best fit.

Also, as already indicated, layers 12 and 16 are preferably of expandable polymeric materials. However, they may be made of other materials such as rigid plastics of which polylactide, polytetrafluoroethylene, polyurethane and acrylic based polymers are but a few examples. Inner layer 12 may be rendered permeable by including openings therein of a size selected to provide any desired flow through rate and diffusion rate. Metals such as stainless steel and nitinol may be used for these layers as well in either a fixed diameter or expandable configuration as is known in the art. Furthermore, the metal and plastic for layers 12 and/or 16 may be in a mesh form, a screen form or a filamentary form as shown for layer 12 in FIG. 3 and may further include collagen or other biological material 13 supported thereon. Examples of such biological materials are shown in the following U.S. Pat. Nos. 4,956,178; 4,902,508; 5,275,826; 5,281,422; 4,950,483; 5,110,064 and 5,024,841. Thickness of such support layers may range over 0.001 inch to 0.010 inch, for example. Such structures in their preferred cylindrical configuration may or may not be sealed at the ends, as described hereinabove.

While this invention may be embodied in many different forms, there are described in detail herein specific preferred embodiments of the invention. This description is an exemplification of the principles of the invention and is not intended to limit the invention to the particular embodiments illustrated. These examples and the description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An implantable device constructed and arranged in a laminate structure comprising:

first and second spaced layers of support material, at least one of said layers being fluid permeable, an intermediate third layer of a matrix material having fluid-swellable characteristics, the intermediate layer being held between the first and second layers, and a drug or therapeutic contained in the intermediate layer, wherein said device upon implantation has a predetermined outer diameter selected to correspond substantially with an inner diameter of an implant site, whereby when the device is implanted in a vessel in a body, the drug or therapeutic is pumped into the vessel in response to the swelling of the fluid-swellable matrix material.

2. The device of claim 1 wherein the first and second layers are comprised of polymeric material.

3. The device of claim 2 wherein the polymeric material is selected from the group consisting of polylactics, polyacetates, polyacrylates, polyglycol, polycaprolactones, polyesters, polyethers, polyamides and mixtures thereof.

4. The device of claim 1 in a cylindrical, stent-like configuration.

5. The device of claim 1 wherein at least one of the first and second layers is comprised of polymeric material.

6. The device of claim 1 wherein the intermediate layer is made of a material selected from the group consisting of polyvinylpyrrolidone, polyethylene glycol, polyethylene oxide or polyvinyl alcohol, said intermediate layer being made up in an aqueous solution containing the dissolved drug or therapeutic to be contained therein.

7. A device as in claim 1 wherein the first and second spaced layers are each comprised of a curable and resorbable material and the intermediate third layer and the drug or therapeutic contained in the intermediate layer are resorbable.

8. An implantable intravascular device having a generally cylindrical form constructed and arranged for blood flow therethrough, said device comprising a multi-layer wall, said wall comprising at least:

an inner binding layer of permeable support material;

an outer binding layer of support material, and an intermediate matrix layer of blood-swellable material, the matrix layer containing therapeutic materials to be dispersed into the blood in response to the swelling of the blood-swellable matrix material, said device upon implantation having a predetermined outer diameter selected to correspond substantially with an inner diameter of an implant site.

9. The device of claim 8 wherein the inner and outer layers of support material are comprised of polymeric material.

10. The device of claim 8 wherein at least one of the inner and outer layers is comprised of polymeric material.

11. The device of claim 10 wherein the at least one polymeric layer is made of a polymeric material selected from the group consisting of polylactics, polyacetates, polyacrylates, polyglycol, polycaprolactones, polyesters, polyethers, polyamides and mixtures thereof.

12. The device of claim 8 wherein the outer layer is comprised of a polymer, a reactive monomer and a polymerization initiator; the intermediate layer is comprised of a swellable drug-bearing layer, and the inner layer is comprised of a porous material.

13. The device of claim 8 wherein:
   a) the outer layer is comprised of a polymeric material selected from the group consisting of polylactics, polyacetates, polyacrylates, polyglycol, polycaprolactones, polyesters, polyethers, polyamides and mixtures thereof, a reactive monomer and a polymerization initiator;
   b) the intermediate layer is comprised of a swellable drug-bearing layer made of a material selected from the group consisting of polyvinylpyrrolidone, polyethylene glycol, polyethylene oxide or polyvinyl alcohol, said intermediate layer being made up in an aqueous solution containing the dissolved drug or therapeutic to be contained therein; and
   c) the inner layer is a porous polymeric material comprising a polymer selected from the group consisting of polylactics, polyacetates, polyacrylates, polyglycol, polycaprolactones, polyesters, polyethers, polyamides and mixtures thereof, a reactive monomer, a polymerization initiator and a component selected from the group consisting of microcrystalline salts, simple inorganic salts, sugars, polysaccharides or mixtures thereof in an effective amount to impart porosity to said inner layer.

14. A device as in claim 8 wherein the inner and outer binding layers are curable and resorbable and the intermediate matrix layer containing therapeutic materials is resorbable.

15. An implantable intravascular device having a generally cylindrical form constructed and arranged for blood flow therethrough, said device comprising a multi-layer wall, said wall comprising at least:
   a) an inner binding layer of permeable support material, said inner layer being comprised of poly-D,L-lactic acid, ethylene glycol dimethacrylate and 2-hydroxy-2-methyl-1-phenyl-1-propanone, and additionally including microcrystalline sodium heparin;
   b) an outer binding layer of support material, said outer layer being comprised of poly-D,L-lactic acid, ethylene glycol dimethacrylate and 2-hydroxy-2-methyl-1-phenyl-1-propanone; and
   c) an intermediate matrix layer of blood-swellable material, the matrix layer containing therapeutic materials to be dispersed into the blood, said intermediate matrix layer being comprised of polyvinylpyrrolidone, water and sodium heparin.

16. An implantable device constructed and arranged in a laminate structure, the device comprising:
   first and second spaced layers of support material, at least one of said layers being fluid permeable,
   an intermediate third layer of a matrix material having fluid-swellable characteristics, the intermediate layer being held between the first and second layers, and
   a drug or therapeutic contained in the intermediate layer, wherein said device has a first outer diameter prior to implantation in a body and a second outer diameter after implantation, and the outer diameter of the device after implantation corresponds substantially with an inner diameter of an implant site,
   whereby when the device is implanted in a body, the drug or therapeutic is pumped into the implant site in response to the swelling of the fluid-swellable matrix material.

17. An implantable device having a generally cylindrical form constructed and arranged for fluid flow therethrough, said device comprising a multi-layer wall, said wall comprising at least:
   an inner binding layer of permeable support material;
   an outer binding layer of support material, and
   an intermediate matrix layer of fluid-swellable material, the matrix layer containing therapeutic materials to be dispersed into an implant site in a body in response to the swelling of the fluid-swellable matrix material, said device having a first outer diameter prior to implantation, and a second outer diameter after implantation, the outer diameter of the device after implantation corresponds substantially with an inner diameter of the implant site.

18. An implantable device constructed and arranged in a laminate structure, comprising:
   first and second spaced layers of support material comprised of poly-D,L-lactic acid, ethylene glycol dimethacrylate and 2-hydroxy-2-methyl-1-phenyl-1-propanone, at least one of which is fluid permeable and is further comprised of microcrystalline sodium heparin,
   an intermediate third of a matrix material having fluid-swellable characteristics, said intermediate layer being comprised of polyvinylpyrrolidone water and sodium heparin, the intermediate layer being held between the first and second layers, and
   a drug or therapeutic contained in the intermediate layer, whereby when the device is implanted in a vessel in a body, the drug or therapeutic is pumped into the vessel in response to the swelling of the fluid-swellable matrix material.

19. An implantable intravascular device having a generally cylindrical form constructed and arranged for blood flow therethrough, said device comprising a multi-layer wall, said wall comprising at least:
   an inner binding layer of permeable support material, said inner layer being comprised of poly-D,L-lactic acid, ethylene glycol dimethacrylate, 2-hydroxy-2-methyl-1-phenyl-1-propanone, and microcrystalline sodium heparin;
   an outer binding layer of support material, said outer layer being comprised of poly-D,L-lactic acid, ethylene glycol dimethacrylate and 2-hydroxy-2-methyl-1-phenyl-1propanone, and
   an intermediate matrix layer of blood-swellable material, the matrix layer being comprised of polyvinylpyrrolidone, water and sodium heparin and further containing therapeutic materials to be dispersed into the blood in response to the swelling of the blood-swellable matrix material.

20. An implantable stent comprising:
   a) first and second spaced layers of support material, at least one of said layers being fluid permeable;
   b) an intermediate third layer of a material having fluid-swellable characteristics, the intermediate layer being held between the first and second layers, said first, second and third layers being constructed and arranged in a laminate structure; and
   c) a drug or therapeutic contained in the intermediate layer,
   wherein said stent upon implantation has an outer diameter adapted to fit an inner diameter of an implant site, whereby when the stent is implanted in a vessel in a body, the drug or therapeutic is pumped into the vessel in response to the swelling of the fluid-swellable material.

21. The implantable stent of claim 20 adapted to be expanded in situ to fit the vessel.

22. The implantable stent of claim 21 wherein the stent is balloon expandable.

23. The implantable stent of claim 21 wherein the stent is self-expanding.

24. The implantable stent of claim 20 wherein at least one of the first and second layers is comprised of polymeric material.

25. The implantable stent of claim 24 wherein the first and second layers are comprised of polymeric material.

26. The implantable stent of claim 24 wherein the polymeric material is selected from the group consisting of polylactics, polyacetates, polyacrylates, polyglycol, polycaprolactones, polyesters, polyethers, polyamides, and mixtures thereof.

27. The implantable stem of claim 20 wherein the intermediate layer is made of a material selected from the group consisting of polyvinylpyrrolidone, polyethylene glycol, polyethylene oxide or polyvinyl alcohol, said intermediate layer being made up in an aqueous solution containing the dissolved drug or therapeutic to be contained therein.

28. A implantable stent of claim 26 wherein the first and second spaced layers are each comprised of a curable and resorbable material and the intermediate third layer and the drug or therapeutic contained in the intermediate layer are resorbable.

29. An implantable intravascular stent having a generally cylindrical form adapted for blood flow therethrough, said stent comprising a multi-layer wall, said wall comprising at least:

an inner binding layer of permeable support material;

an outer binding layer of support material, and an intermediate layer of blood-swellable material, the intermediate layer containing therapeutic materials to be dispersed into the blood in response to the swelling of the blood-swellable material, said stent upon implantation having an outer diameter adapted to fit an inner diameter of an implant site.

30. The stent of claim 29 adapted to be expanded to fit the implant site.

31. The stent of claim 30 which is balloon expandable.

32. The stent of claim 30 which is self-expanding.

33. The stent of claim 29 wherein the inner and outer layers of support material are comprised of polymeric material.

34. The stent of claim 29 wherein at least one of the inner and outer layers is comprised of polymeric material.

35. The stent of claim 34 wherein the at least one polymeric layer is made of a polymeric material selected from the group consisting of polylactics, polyacetates, polyacrylates, polyglycol, polycaprolactones, polyesters, polyethers, polyamides and mixtures thereof.

36. The stent of claim 29 wherein:

a) the outer layer is comprised of a polymeric material selected from the group consisting of polylactics, polyacetates, polyacrylates, polyglycol, polycaprolactones, polyesters, polyethers, polyamides and mixtures thereof, a reactive monomer and a polymerization initiator;

b) the intermediate layer is comprised of a swellable drug-bearing layer made of a material selected from the group consisting of polyvinylpyrrolidone, polyethylene glycol, polyethylene oxide or polyvinyl alcohol, said intermediate layer being made up in an aqueous solution containing the dissolved drug or therapeutic to be contained therein; and c) the inner layer is a porous polymeric material comprising a polymer selected from the group consisting of polylactics, polyacetates, polyacrylates, polyglycol, polycaprolactones, polyesters, polyethers, polyamides and mixtures thereof, a reactive monomer, a polymerization initiator and a component selected from the group consisting of microcrystalline salts, simple inorganic salts, sugars, polysaccharides or mixtures thereof in an effective amount to impart porosity to said inner layer.

37. A stent as in claim 29 wherein the inner and outer binding layers are curable and resorbable and the intermediate matrix layer containing therapeutic materials is resorbable.

38. The stent of claim 29 wherein the outer layer is comprised of a polymer, a reactive monomer and a polymerization initiator; the intermediate layer is comprised of a swellable drug-bearing layer, and the inner layer is comprised of a porous material.

39. An implantable intravascular stent having a generally cylindrical form constructed and arranged for blood flow therethrough, said stent comprising a multi-layer wall, said wall comprising at least:

a) an inner binding layer of permeable support material, said inner layer being comprised of poly-D,L-lactic acid, ethylene glycol dimethacrylate and 2-hydroxy-2-methyl-1-phenyl-1-propanone, and additionally including microcrystalline sodium heparin;

b) an outer binding layer of support material, said outer layer being comprised of poly-D,L-lactic acid, ethylene glycol dimethacrylate and 2-hydroxy-2-methyl-1-phenyl-1-propanone; and c) an intermediate layer of blood-swellable material, the intermediate layer containing therapeutic materials to be dispersed into the blood, said intermediate layer being comprised of polyvinylpyrrolidone, water and sodium heparin.

40. The stent of claim 39 adapted to be expanded to fit the implant site.

41. The stent of claim 40, said stent being balloon expandable.

42. The stent of claim 40, said stent being self-expanding.

43. An implantable stent comprising:

first and second spaced layers of support material, at least one of said layers being fluid permeable, an intermediate third layer having fluid-swellable characteristics, the intermediate layer being held between the first and second layers, and a drug or therapeutic contained in the intermediate third layer, wherein said stent has a first outer diameter prior to implantation in a body and a second outer diameter after implantation, and the outer diameter of the stent after implantation corresponds substantially with an inner diameter of an implant site, whereby when the stent is implanted in a body, the drug or therapeutic is pumped into the implant site in response to the swelling of the fluid-swellable intermediate third layer.

44. The stent of claim 43 adapted to be expanded to fit the implant site.

45. The stent of claim 44 which is balloon expandable.

46. The stent of claim 45 which is self-expanding.

47. An implantable stent having a generally cylindrical form and being adapted for fluid flow therethrough, said stent comprising a multi-layer wall, said wall comprising at least:

an inner binding layer of permeable support material;

an outer binding layer of support material, and an intermediate layer of fluid-swellable material, the intermediate layer containing therapeutic materials to be dispersed into an implant site in a body in response to the swelling of the fluid-swellable material, said stent having a first outer diameter prior to implantation, and a second outer diameter after implantation, wherein the outer diameter of the stent after implantation corresponds substantially with an inner diameter of the implant site.

48. The stent of claim 47 adapted to be expanded to fit the implant site.

49. The stent of claim 48 which is balloon expandable.

50. The stent of claim 48 which is self-expanding.

51. An implantable stent comprising:

first and second spaced layers of support material comprised of poly-D,L-lactic acid, ethylene glycol dimethacrylate and 2-hydroxy-2-methyl-1-phenyl-1-propanone, at least one of which is fluid permeable and is further comprised of microcrystalline sodium heparin, an intermediate third layer having fluid-swellable characteristics, said intermediate layer being comprised of polyvinylpyrrolidone, water and sodium heparin, the intermediate layer being held between the first and second layers, and a drug or therapeutic contained in the intermediate layer, whereby when the stent is implanted in a vessel in a body, the drug or therapeutic is pumped into the vessel in response to the swelling of the fluid-swellable material.

52. The stent of claim 51 adapted to be expanded to fit the implant site.

53. The stent of claim 52 which is balloon expandable.

54. The stent of claim 52 which is self-expanding.

55. An implantable intravascular stent having a generally cylindrical form adapted for blood flow therethrough, said stent comprising a multi-layer wall, said wall comprising at least:

an inner binding layer of permeable support material, said inner layer being comprised of poly-D,L-lactic acid, ethylene glycol dimethacrylate, 2-hydroxy-2-methyl-1-phenyl-1-propanone, and microcrystalline sodium heparin;

an outer binding layer of support material, said outer layer being comprised of poly-D,L-lactic acid, ethylene glycol dimethacrylate and 2-hydroxy-2-methyl-1-phenyl-1-propanone, and an intermediate layer of blood-swellable material, the intermediate layer being comprised of polyvinylpyrrolidone, water and sodium heparin and further containing therapeutic materials to be dispersed into the blood in response to the swelling of the blood-swellable material.

56. The stent of claim 55 adapted to be expanded to fit the implant site.

57. The stent of claim 56 which is balloon expandable.

58. The stent of claim 56 which is self-expanding.

* * * * *